(12) United States Patent
Demmer et al.

(10) Patent No.: US 8,969,094 B2
(45) Date of Patent: Mar. 3, 2015

(54) METHOD FOR QUALIFYING A NON-PARTICULATE ION-EXCHANGER ADSORBER

(75) Inventors: Wolfgang Demmer, Goettingen (DE); Rene Faber, Goettingen (DE); Hans-Heinrich Hoerl, Bovenden (DE); Axel Thiefes, Hardegsen (DE)

(73) Assignee: Sartorius Stedim Biotech GmbH (DE)

( * ) Notice: Subject to any disclaimer, the term of this patent is extended or adjusted under 35 U.S.C. 154(b) by 365 days.

(21) Appl. No.: 13/517,153

(22) PCT Filed: Nov. 10, 2010

(86) PCT No.: PCT/EP2010/006853
§ 371 (c)(1),
(2), (4) Date: Jun. 19, 2012

(87) PCT Pub. No.: WO2011/082727
PCT Pub. Date: Jul. 14, 2011

(65) Prior Publication Data
US 2012/0276652 A1    Nov. 1, 2012

(30) Foreign Application Priority Data

Jan. 8, 2010 (DE) .......................... 10 2010 004 188

(51) Int. Cl.
*G01N 31/16* (2006.01)
*G01N 30/88* (2006.01)
*G01N 30/96* (2006.01)

(52) U.S. Cl.
CPC .............. *G01N 30/88* (2013.01); *G01N 30/96* (2013.01); *G01N 2030/889* (2013.01)
USPC ........................................................ 436/163

(58) Field of Classification Search
None
See application file for complete search history.

(56) References Cited

U.S. PATENT DOCUMENTS

| 7,281,410 B2 | 10/2007 | Phillips |
| 2003/0089664 A1 | 5/2003 | Phillips |
| 2008/0299672 A1 | 12/2008 | Nochumson et al. |
| 2011/0147292 A1 | 6/2011 | Demmer et al. |
| 2011/0163029 A1 | 7/2011 | Faber et al. |

FOREIGN PATENT DOCUMENTS

| DE | 195 45 371 | 5/1997 |
| DE | 10 2008 018 732 | 10/2009 |
| DE | 10 2008 055 821 | 10/2009 |

OTHER PUBLICATIONS

English translation of the International Preliminary Report on Patentability, Jul. 10, 2012.
Product data sheet—"Sartobind Ion Exchange MA Units", 2010.
Lendro et al.—"Characterization of ion exchange stationary phases via pH transition profiles"—Journal of Chromatography A, 1185 (2008) pp. 59-70.
Reif et al.—"Characterization and application of strong ion-exchange membrane adsorbers as stationary phases in high-performance liquid chromatography of proteins"—Journal of Chromatography A, 654 (1993) pp. 29-41.
Hahn et al.—"Control method for integrity of continuous beds"—Journal of Chromatography A, 908 (2001) pp. 179-184.

(Continued)

*Primary Examiner* — Robert Xu
(74) *Attorney, Agent, or Firm* — Gerald E. Hespos; Michael J. Porco; Matthew T. Hespos

(57) ABSTRACT

The present invention relates to a method for the validation of a non-particulate ion exchange adsorber and a kit for the validation of a non-particulate ion exchange adsorber.

4 Claims, 4 Drawing Sheets

(56) References Cited

OTHER PUBLICATIONS

Santarelli et al.—"Characterization and application of new macroporous membrane ion exchangers"—Journal of Chromatography B, 706 (1998) pp. 13-22.

Podgornik et al.—"Construction of Large-Volume Monolithic Columns"—Analytical Chemistry, Nov. 15, 2000, vol. 72, No. 22, pp. 5693-5699.

Lendero et al.—"Simple method for determining the amount of ion-exchange groups on chromatographic supports"—Journal of Chromatography A, 1065 (2005) pp. 29-38.

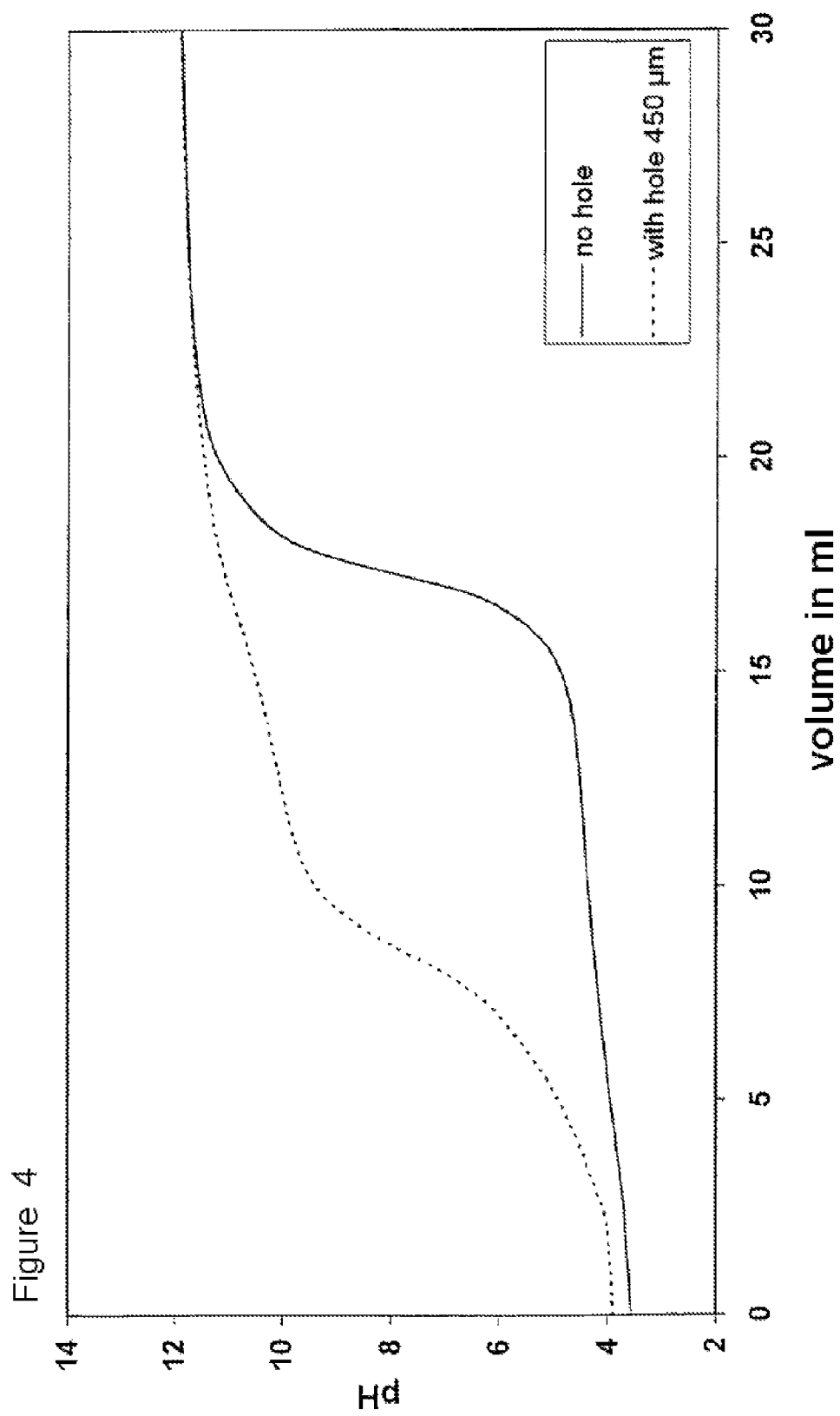

US 8,969,094 B2

METHOD FOR QUALIFYING A NON-PARTICULATE ION-EXCHANGER ADSORBER

BACKGROUND OF THE INVENTION

1. Field of the Invention

The present invention relates to a method for the validation of a non-particulate ion exchange adsorber and a kit for the validation of a non-particulate ion exchange adsorber.

2. Description of the Related Art

The present invention is based on the definitions described below. "Adsorptive substance separation" is understood to mean the separation of one or more components from a fluid phase by selective adsorption of this/these component(s) on a solid phase, the "adsorbent" (plural "adsorbents"). The field of the invention relates to substance separation in liquids, the liquid being called the "medium" below and the device in which the adsorption is performed the "adsorber". Adsorbents are porous solids which via functional surface groups, which are called "ligands", can selectively enter into bonds with certain components of fluids. As well as the long known "particulate" adsorbents, also called chromatography gels, other "non-particulate adsorbents" have become established, which are based on a matrix of an entirely different nature. These are so-called monolithic adsorbents consisting of a three-dimensional porous solid or support based on microporous membranes of various polymers. Two-dimensional adsorbents with the pores passing from one side to the other are described as adsorption membranes. According to the invention, target substance(s) and/or contaminant(s) are described as "adsorband" and used in the singular, although they can also consist of several different substances. The "capacity" of an adsorbent is understood to mean a quantitative measure for its uptake capacity for adsorband. The capacity is based on a defined quantity of adsorbent.

The present invention concerns non-particulate ion exchange adsorbers. Some examples are mentioned below. In the state of the art, various non-particulate anion and cation exchangers are known. As examples, strong anion exchangers based on adsorption membranes such as Sartobind® Q from Sartorius Stedim Biotech GmbH, Mustang® Q from Pall Corp., Q Membrane from Natrix Separations or monoliths such as CIM® QA from BIA Separations are mentioned. Other examples are weak anion exchangers such as Sartobind® D from Sartorius Stedim Biotech GmbH, Chromasorb® from Millipore or CIM® EDA from BIA Separations. Furthermore, negatively charged adsorption membranes, such as the strong cation exchanger Sartobind® S or the weak cation exchanger Sartobind® C from Sartorius Stedim Biotech GmbH, strong cation exchange membranes Mustang® S from Pall Corp., S Membrane from Natrix Separations or strong cation exchangers based on monoliths such as for example CIM® SO3 or weak cation exchangers based on monoliths such as for example CIM® CM from BIA Separations are known in the state of the art.

The capacity of an ion exchanger is understood to mean a quantitative measure for its uptake capacity for exchangeable counter-ions. A distinction must be made between the total capacity and the usable capacity. While the total capacity states the total quantity of exchangeable counter-ions, the usable capacity relates only to that fraction which can be utilized under the particular operating conditions (e.g. pH of the solution, concentration of the solution, nature of the counter-ions). Adsorbands can be single molecules, associations or particles, which are preferably proteins or other substances of biological origin. Target substances can for example be recombinant proteins, such as for example monoclonal antibodies. Contaminants can for example be viruses, proteins, amino acids, nucleic acids, endotoxins, protein aggregates, ligands or parts thereof. The removal of contaminants the absence whereof is necessary or desirable for technical, regulatory or other reasons is described as "negative adsorption".

Most contaminant removal applications are at present operated with conventional chromatography gels. These are particulate in form and are operated in the form of packings in columns. After filling of the column with the medium, a test for function and integrity follows. For this, the theoretical plate number/HETP and the asymmetry of the column packing are determined with suitable solutions of non-binding molecules such as acetone or cooking salt. On the basis of reference samples, the quality of the column packing and suitability for the chromatography step can be determined. The chromatography columns are markedly overdimensioned in order to achieve adequate flow rates. The columns are reused, which signifies considerable cleaning and validation expenditure.

The implementation of chromatographic separations by means of adsorption membranes is also called membrane chromatography. The term adsorption membrane should be understood as a general term for various types of adsorption membranes, such as ion exchange membranes, affinity membranes, hydrophobic membranes or activated membranes. Since filtration effects are most likely undesired, the pore sizes of the adsorptive membranes used on the industrial scale mostly lie in the range of >0.4 µm. In contrast to particulate adsorbents, adsorption membranes offer the possibility of forcing medium volume flow by application of a hydraulic pressure difference between the two sides of their surface, whereby instead of purely diffusive transport of the adsorband in the direction of a concentration gradient into the inside of the adsorbent, convective material transport is attained, which can take place very much faster with high volume flow rate. Thereby a disadvantage inherent to the particulate adsorbents, which is described as "diffusion limitation", which consists in that with increasing adsorband particle size and increasing adsorband molecular mass the time necessary for establishment of the adsorption equilibrium increases considerably, which results in a worsening of the kinetics, can be avoided. Because of the described advantages of adsorption membranes, these are preferably used in processes wherein the adsorband is present in the medium in very low concentration relative to the capacity of the matrix, so that a large volume of the medium can be processed per unit area of the adsorbent before exhaustion of its capacity.

Typical applications are in the field of negative adsorption, e.g. the removal of contaminants such as DNA, viruses, host cell proteins (HCP), CHOP (Chinese hamster ovary proteins) and/or endotoxins from antibody-containing solutions with positively charged adsorption membranes. This can (may) proceed irreversibly if the adsorbent is to be used only once. The breakthrough of contaminants is a critical factor in validated biopharmaceutical processes. The host cell proteins represent a broad spectrum of different cell proteins with different isolectric points (pI) and different size and affinity to the adsorbent. The concentration and composition of the contaminants depend on the expression system and on the upstream purification steps. Typical concentrations of host cell proteins in a protein A pool lie in the range 500-5000 ppm (ng/mg antibody) and in the range 50-500 ppm after a further CEX step (cation exchange step). The virus depletion is stated as the LRV (log reduction value). It corresponds to the negative base ten logarithm of the ratio of the virus concentration in the starting medium to the virus concentration in the filtrate. Hence an LRV of 5 means that 99.999% of the viruses have been removed by the adsorber. Similarly, the depletion of endotoxins is stated as the LRV.

Adsorption membranes are in general used in modules/capsules which are also described as "membrane adsorbers". They consist of a housing in which mostly one or preferably several layers of an adsorption membrane are installed. The adsorption membrane is sealed in the housing such that the flow is obligatorily through the membrane layers. The types resemble the modules customary in membrane filtration (e.g. wound module, stack module, etc.). The adsorber is as a rule supplied ready for connection, hence packing of the adsorber by the user is no longer necessary. The design and the shape of membrane adsorbers is adapted to the rapid mode of operation compared to the particulate chromatography columns. In the case of membrane adsorbers, the ratio of adsorption membrane stack height to incident flow area is orders of magnitude smaller than with chromatography columns. The quantities of adsorption membranes needed are as a rule markedly below those of chromatography gels. As a result, the influence of the dead volumes and the adsorber periphery (tubes, pipes, connections, detectors) is also greater than with conventional chromatography columns. The validation methods used for chromatography, such as the determination of the plate number/HETP or the asymmetry of the column packing, are thus rather insensitive and only usable for membrane adsorbers to a very limited extent.

The following criteria should be fulfilled and documented in the validation of an adsorbent installed in the process so that operation appropriate for the application is ensured and the regulatory requirements are fulfilled:

A. Are the correct functional groups present?
B. Is a sufficient quantity of functional groups present?
C. Is a sufficient quantity of functional groups attained during operation of the adsorbent?
D. Is the membrane structure, the membrane stack and the attachment of the membrane to the housing fault-free?

If all these four criteria are fulfilled for an adsorber, according to the invention the integrity of this adsorber is established.

Central to the validation of membrane adsorber systems by the manufacturer are measurements of different parameters, such as for example volume flow rate, binding capacity for model molecules, ligand density, mechanical stability, chemical compatibility and extractable substances. Analogously to the columns, the corresponding tests for functionality and integrity must also be conducted with the membrane adsorbers.

One of the methods used is an integrity test by means of a test device which was developed for sterile-filtering flat filters and filter candles. An example of a commercially available device is the Sartocheck® 4 from Sartorius Stedim Biotech GmbH. Here, the diffusion of air through a membrane stack wetted with water is determined and compared with an intact reference membrane stack. If the diffusion is above a predefined reference value, then a defect is present in the membrane stack. However, this method only yields information about the point D stated above and hence is only valid to a limited extent.

In one method (U.S. Pat. No. 7,281,410 B2, Oct. 16, 2007, Phillips, "Method for determining an effective Peclet number for a membrane device" and US Patent Application Publication US 2003/0089664 A1, May 15, 2003, Phillips, "Membrane Adsorber Device"), the determination of the Peclet number of a membrane adsorber is effected by the steps a) equilibration of the membrane adsorber with an equilibration buffer, b) loading of the membrane adsorber with a known concentration of a specific adsorband in an equilibration buffer, c) detection of the breakthrough of the adsorband as a function of time, loading volume and other suitable variables which are linked with the quantity of the adsorband loaded, d) analysis of the breakthrough curve in order to determine the relevant flow characteristics of the membrane adsorber by calculation of the sharpness of the breakthrough curve, and e) comparison of the results from step d) with a known intact membrane adsorber in order to determine the effective Peclet number. As the adsorband, for example tosylglutamic acid is used, the breakthrough whereof is detected by detection of the UV absorption.

A further method (US Patent Application Publication US 2008/0299672 A1, Dec. 4, 2008, Nochumson et al., "System and method for testing chromatography media and devices") describes a method for the determination of the integrity of a chromatography membrane welded into a housing, wherein the membrane is subjected to pulsed application of an adsorband e.g. adenosine monophosphate (AMP) under standard conditions, then the bound AMP is eluted with buffer solution and the concentration of the AMP in the eluate as a function of time is measured by UV absorption at 260 nm. The extinction coefficient-time curve thus obtained is compared with the extinction coefficient-time curve of an intact reference module. On occurrence of a defect (hole), in contrast to the intact reference module, early UV absorption occurs.

Both methods known in the state of the art use a "non-process" organic adsorband which is first adsorbed onto the adsorbent in a suitable buffer. In the method according to US 2008/0299672 A1, the adsorband must be eluted from the adsorbent. This represents a major and decisive disadvantage, since it must always be shown that the adsorband has been fully removed from the adsorbent and from the process medium or product. In some cases, the adsorband must be removed in a downstream process step. For regulatory, economic and process safety reasons, this represents a significant limitation. Further, the methods exhibit a relatively low sensitivity of detection via UV absorption and hence exhibit relatively low precision.

For ion exchangers, a pH titration curve (pH of the solution as a function of the quantity of alkali solution or acid added) give information about the number and the pK of the active groups. In a direct pH titration, a defined quantity of ion exchanger with or without addition of salt is titrated directly with equilibrated alkali solution or acid and the pH of the solution is measured after each addition. After each addition of alkali solution or acid, establishment of the equilibrium between ion exchanger and solution must be awaited. This can take a few hours to weeks. In Journal of Chromatography A, 1065 (2005) 29-38, a method for the determination of the quantity of ion exchange groups on a chromatography support is described. After saturation of the adsorbent with a concentrated buffer solution, a low concentration buffer solution at the same pH is passed through the adsorbent. It could be shown that the change in pH with time is a measure of the number of charged groups on the adsorbent. However, the pH change lies in the range of max. 1 pH step and hence this method is insensitive for the detection of faults in membrane adsorbers in the context of a validation.

The present invention is based on the objective of providing a validation method for non-particulate ion exchange adsorbers which enables highly sensitive, robust, simple, non-destructive testing of their integrity and functionality. Preferably, aids (e.g. measuring instruments, test solutions) which signify no impairment of the function of the adsorbent or the product quality nor require any additional process steps or chemicals should be used for the validation.

SUMMARY OF THE INVENTION

Specifically, the invention describes a method which can detect faults or defects in non-particulate ion exchange adsorbers by simple means, robustly, non-destructively and with very high sensitivity.

According to the present invention, the method for validation of a non-particulate ion exchange adsorber with anion-exchanging or cation-exchanging groups comprises the steps of a) loading of the non-particulate ion exchange adsorber with alkali solution in the case of an anion exchanger or loading of the non-particulate ion exchange adsorber with acid in the case of a cation exchanger, b) rinsing of the non-particulate ion exchange adsorber with water, c) loading of the non-particulate ion exchange adsorber with a liquid, ion-containing medium with detection of the concentration of the ions that have broken through by means of an ion-sensitive probe, and d) comparison of the concentration profile detected in step c) with that of a non-particulate ion exchange adsorber of known integrity.

The present invention and further advantages deriving there-from are explained in more detail in the following description with reference to the embodiments described in the examples.

For example for the case of a non-particulate, strong anion exchange adsorber with quaternary ammonium ligands, according to the present invention 1 mol/l NaOH solution in excess is first passed through the anion exchanger. The anion exchanger is thereby loaded with $OH^-$ ions. The anion exchanger is now briefly washed with water in order to displace the free alkali solution from the anion exchanger, until the outflow exhibits a low conductivity. On passing acid (e.g. 10 mmol/l HCl) through, the ion exchange proceeds. The released $OH^-$ ions combine with the $H^+$ ions of the acid to give water. The $Cl^-$ ions are practically completely taken up by the anion exchanger as long as this still contains $OH^-$ ions. At the same time, the conductivity and the pH in the outflow initially remain almost unchanged, since until the breakthrough of the acid practically all $H^+$ ions are neutralized by released $OH^-$ ions. As soon as the anion exchanger has released all $OH^-$ ions, the pH in the outflow falls steeply. The usable capacity or breakthrough capacity of the anion exchanger can be calculated from the consumption of the acid.

Furthermore, for example for the case of a non-particulate, weak anion exchange adsorber with for example polyallylamine ligands according to the present invention, 1 mol/l NaOH solution in excess is first passed through the anion exchanger. The anion exchanger is thereby converted to free $NH_2$ amino groups. The anion exchanger is now briefly washed with water in order to displace the free alkali solution from the adsorber, until the outflow exhibits a low conductivity. On passing acid (e.g. 10 mmol/l HCl) through, the $NH_2$ groups with the $H^+$ ions of the acid are converted into $NH_3^+$ groups. At the same time, the $Cl^-$ ions are practically completely taken up by the anion exchanger. The conductivity and the pH in the outflow initially remain almost unchanged, since until the breakthrough of the acid practically all $H^+$ ions are bound by free $NH_2$ groups. As soon as all $NH_2$ groups of the anion exchanger are saturated with $H^+$ ions, the pH in the outflow falls steeply. The usable capacity or breakthrough capacity of the anion exchanger can be calculated from the consumption of the acid.

In addition, for example for the case of a non-particulate, strong cation exchange adsorber with sulfonic acid ligands, according to the present invention 1 mol/l HCl solution in excess is first passed through the cation exchanger. The cation exchanger is thereby loaded with $H^+$ ions. The cation exchanger is now briefly washed with water in order to displace the free acid from the adsorber, until the outflow exhibits a low conductivity. On passing alkali solution (e.g. 10 mmol/l NaOH) through, the ion exchange proceeds. The released $H^+$ ions combine with the $OH^-$ ions of the alkali solution to give water. The $Na^+$ ions are practically completely taken up by the cation exchanger as long as this still contains $H^+$ ions. At the same time, the conductivity and the pH in the outflow initially remain almost unchanged, since until the breakthrough of the alkali solution practically all $OH^-$ ions are neutralized by released $H^+$ ions. As soon as the cation exchanger has released all $H^+$ ions, the pH in the outflow rises steeply. The usable capacity or breakthrough capacity of the cation exchanger can be calculated from the consumption of the alkali solution.

According to the present invention, when the liquid, ion-containing medium is present as alkali solution, for example sodium hydroxide solution or potassium hydroxide solution can be used. Conversely, when the liquid, ion-containing medium is present as acid, for example hydrochloric acid, sulfuric acid or acetic acid can be used in the present invention. According to the present invention, the concentrations can be selected depending on the ion exchange capacity of the adsorber. Concentrations of <1 mol/l, preferably <0.5 mol/l and particularly preferably of <0.1 mol/l can be used.

According to the present invention, the ion-sensitive probe for the detection of the concentrations of the ions that have broken through is preferably a pH electrode, an ion-sensitive field effect transistor or a pH indicator dye. Here according to the invention the determination of the ion concentration can for example be effected by means of a suitable flow cell with different simultaneously measuring sensors and the corresponding electronic circuit modules. The detection can be carried out directly on/in the adsorber by incorporation of suitable ion-sensitive probes known to those skilled in the art. In the case of hydrogen ions or hydroxide ions, the following are mentioned as examples of such probes:

potentiometric indicator electrodes, e.g. glass electrodes, ion-sensitive field effect transistors or
pH indicator dyes.

Other examples of ion-sensitive probes for the detection of inorganic ions are listed in Table 1.

TABLE 1

Examples of ion-sensitive electrodes and ions to be detected

| Manufacturer | Ions | Sensitivity in mol/l |
|---|---|---|
| Endress & Hauser | $NH_4^+$ | no info. |
|  | $NO_3^-$ | no info. |
| Mettler Toledo | $Na^+$ | $10^{-7}$ |
|  | $Cl^-$ | $10^{-5}$ |
|  | $K^+$ | $10^{-6}$ |
|  | $Ca^{2+}$ | $10^{-6}$ |
|  | $NO_3^-$ | $10^{-5}$ |
| Metrohm | $Na^+$ | $10^{-6}$ |
|  | $Cl^-$ | $5 \times 10^{-7}$ |
|  | $K^+$ | $10^{-6}$ |
|  | $Ca^{2+}$ | $5 \times 10^{-7}$ |
|  | $NH_4^+$ | 0.1-17,000 ppm |

According to the present invention, for example disposable sensors can be used, which after the use of the adsorber can be discarded together with this.

In case of damage and/or a fault in the manufacture of a non-particulate ion exchange adsorber, the change in the ion concentration in the outflow and its characteristics shift such that this takes place sooner, since the retention capacity of the adsorber is impaired. Surprisingly and advantageously, according to the present invention, owing to the sensitivity of the method this can be detected even with only slight impairment of the adsorber. This was not hitherto possible with UV absorption, although such an undetected defect nonetheless resulted in a deterioration for example in virus retention and hence undetectedly the performance of the shaped body was possibly inadequate for such an application.

Advantageously, very small faults and defects can be detected according to the method of the present invention simply and continuously. As a result, the retention capacity for contaminants, such as for example viruses, DNA, host cell proteins and endotoxins, can advantageously be tested with this method.

According to the invention, the equilibration for the relevant process step follows directly after the validation of the adsorber. The method according to the invention can advantageously be performed before ("pre-use") and/or after ("post-use") the use of the adsorber. Furthermore, some process steps, such as for example disinfection of the adsorber with alkali solution, can be integrated into the validation method according to the invention, in that for example with an anion exchanger the first step is performed under disinfection conditions with 1 mol/l NaOH for 30 mins. Similarly, the regeneration step after the use of the adsorber, for example with 1 mol/l NaOH at elevated temperature, can be integrated into the method according to the invention.

Finally, the present invention provides a kit for the validation of a non-particulate ion exchange adsorber, which enables highly sensitive, robust, simple, non-destructive testing of its integrity and functionality.

BRIEF DESCRIPTION OF THE DRAWINGS

FIGS. 1 to 4 show breakthrough curves which are explained below in more detail in Examples 1 to 4.

Here FIG. 1 shows breakthrough curves on a strong anion exchange membrane adsorber stack (3-layer) with quaternary ammonium ligands with and without artificial faults, hole sizes 440 µm and 600 µm.

FIG. 2 shows breakthrough curves on a weak anion exchange membrane adsorber stack (3-layer) with polyallylamine ligands with and without artificial fault (hole size 450 µm) on application of sulfuric acid.

FIG. 3 shows breakthrough curves on a weak anion exchange membrane adsorber stack (3-layer) with polyallylamine ligands with and without artificial fault (hole size 450 µm) on application of hydrochloric acid.

FIG. 4 shows breakthrough curves on a strong cation exchange membrane adsorber stack (3-layer) with sulfonic acid ligands with and without artificial faults (hole size 450 µm) on application of sodium hydroxide solution.

DETAILED DESCRIPTION OF THE PREFERRED EMBODIMENTS

The present invention and further advantages deriving there-from are explained in more detail in the following description with reference to the embodiments described in the examples.

EXAMPLES

Example 1

Breakthrough Curves on a Strong Anion Exchange Adsorber With Quaternary Ammonium Ligands With and Without Various Defects A commercially available membrane of the Sartobind® Q type, a strong anion exchanger, order No. 94IEXQ42-001, from Sartorius Stedim Biotech GmbH, was used. Three membrane disks with a diameter of 3 cm were punched out of a flat membrane sheet, laid into a 3-layer stack, placed in a clamping device in a suitable housing and integrated into a chromatography system, type ÄKTA Prime plus from General Electric Healthcare. The overall membrane area is 15 cm$^2$, and the inflow area 5 cm$^2$. The system was operated according to the manufacturer's instructions. All steps were performed at a flow rate of 10 ml/min. For the simulation of various defects in this membrane stack, before installation, holes with the diameters 450 µm or 600 µm were punched in the dry membrane stack, using injection needles with flat-ground tips. Because of the flexible membrane matrix, the size and shape of the defects are not strictly defined. The following steps were performed:
1. Rinsing of the adsorbent with 10 ml of a solution of 1 mol/l NaOH in water.
2. Washing of the adsorbent with 40 ml of high purity water from a unit of the Arium® type from Sartorius Stedim Biotech GmbH.
3. Application of a 2 mmol/l $H_2SO_4$ solution onto the adsorber.
4. Recording of the volume passed and the pH in the outflow by means of a flow cell for the pH.

Figure 1:
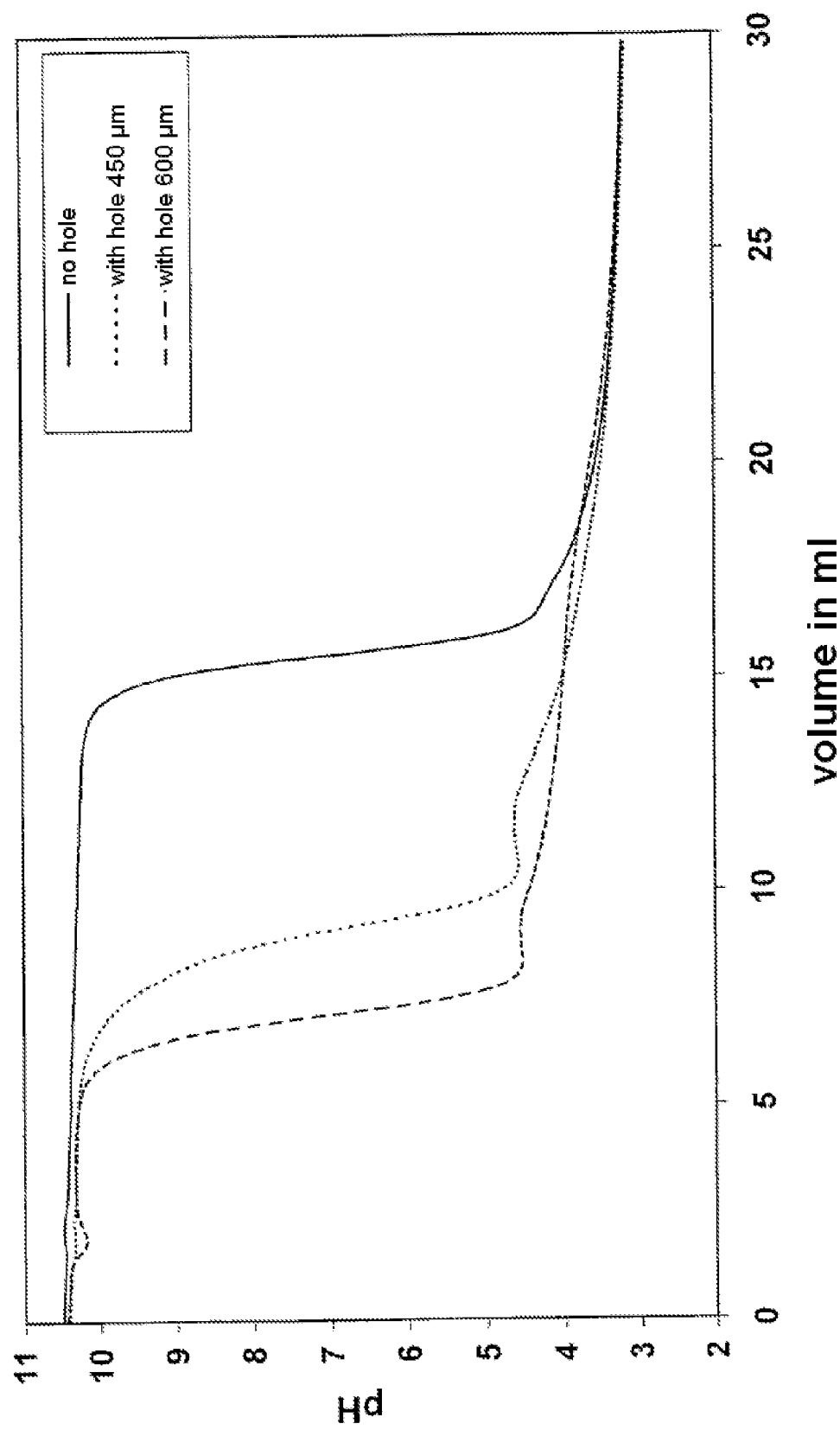

FIG. 1 shows breakthrough curves of 3-layer ion exchange membrane adsorber stacks with quaternary ammonium ligands in which artificial defects (holes) had been introduced, compared to an intact stack, on application of sulfuric acid. A markedly earlier breakthrough is seen for the membrane stack with hole compared to the intact membrane stack. A differentiation of the different hole sizes can also be discerned.

Example 2

Breakthrough Curves on Non-Particulate, Weak Anion Exchange Adsorbers With Polyallylamine Ligands on Application of Sulfuric Acid A membrane modified with polyallylamine, prepared as described in WO2009/127285 A1 (example 21), was installed in a housing and used as described in Example 1 of this application. The following steps were performed:
1. Rinsing of the adsorbent with 10 ml of a solution of 1 mol/l NaOH in water.
2. Washing of the adsorbent with 40 ml of high purity water.
3. Application of a 10 mol/l $H_2SO_4$ solution onto the adsorber.
4. Recording of the volume passed and the pH in the outflow by means of a flow cell for the pH.

Figure 2:
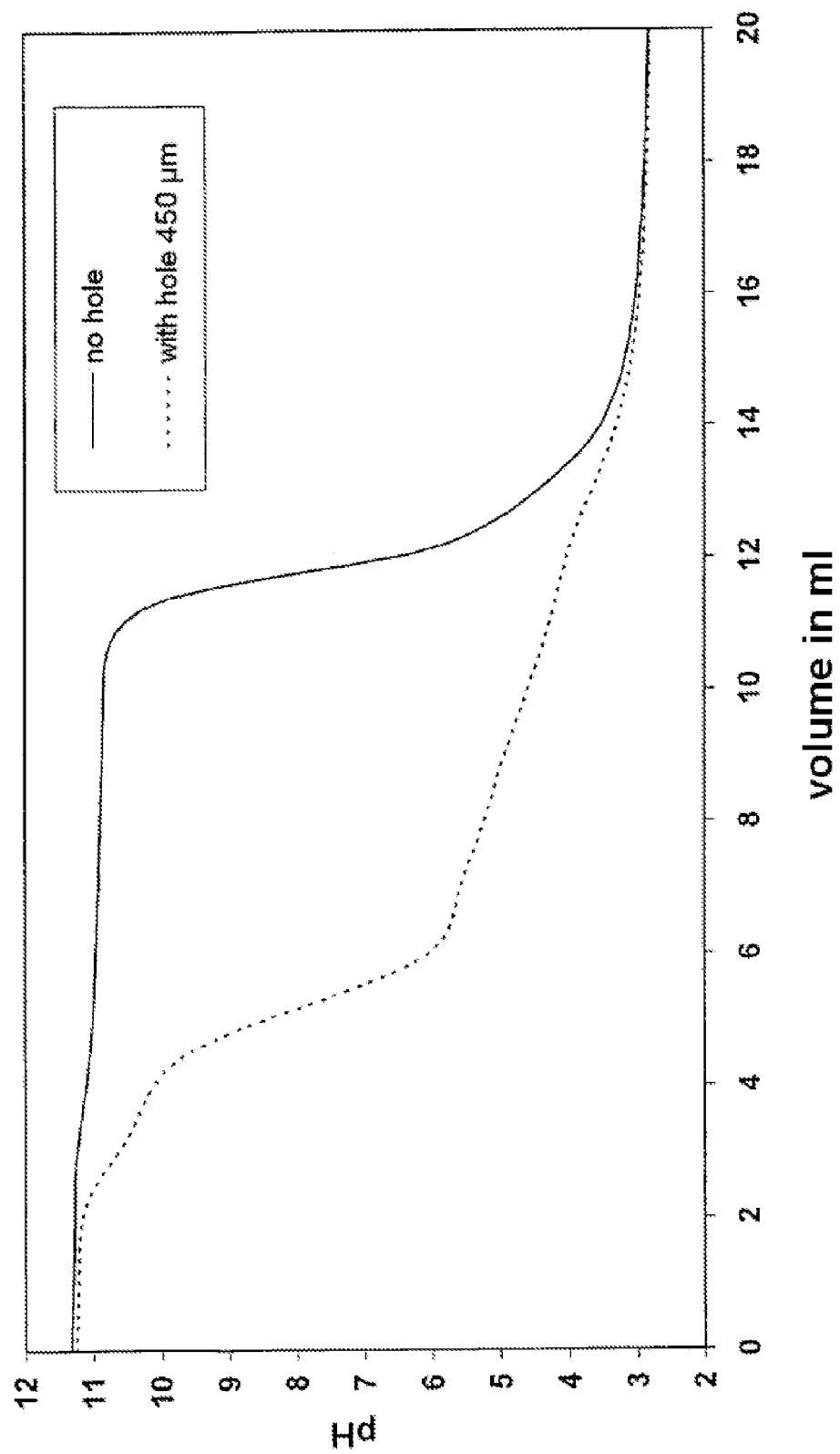

FIG. 2 shows the breakthrough curve on a 3-layer weak ion exchange adsorber stack with polyallylamine ligands in which an artificial defect (hole) had been introduced, compared to an intact stack, on application of sulfuric acid. A markedly earlier breakthrough is seen for the membrane stack with hole compared to the intact membrane stack.

Example 3

Breakthrough Curves on Non-Particulate, Weak Anion Exchange Adsorbers With Polyallylamine Ligands on Application of Hydrochloric Acid A membrane modified with polyallylamine, prepared as described in WO2009/127285 A1 (example 21), was installed in a housing and used as described in Example 1 of this application. The following steps were performed:
1. Rinsing of the adsorbent with 10 ml of a solution of 1 mmol/l NaOH in water.
2. Washing of the adsorbent with 40 ml of high purity water.
3. Application of a 10 mmol/l HCl solution onto the adsorber.
4. Recording of the volume passed and the pH in the outflow by means of a flow cell for the pH.

Figure 3:
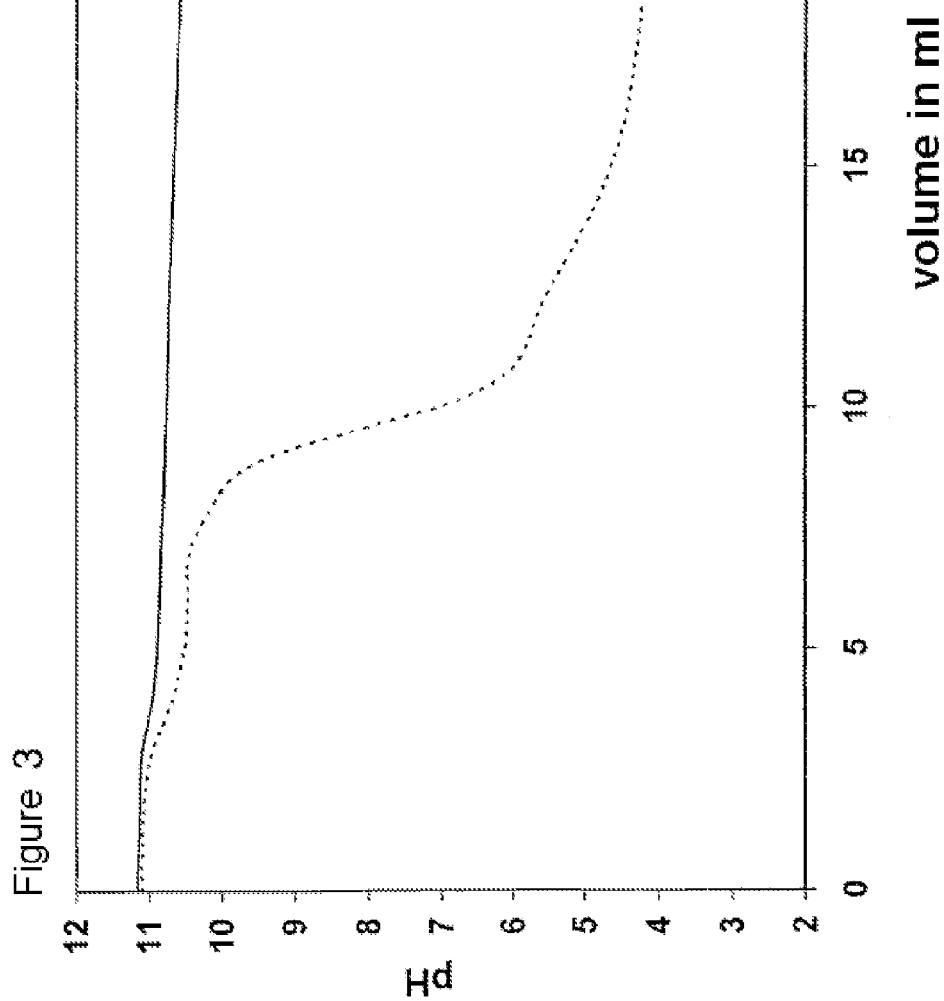

FIG. 3 shows the breakthrough curve of a 3-layer weak ion exchange adsorber stack with polyallylamine ligands in which an artificial defect (hole) had been introduced, compared to an intact stack, on application of hydrochloric acid. A markedly earlier breakthrough is seen for the membrane stack with hole compared to the intact membrane stack.

Example 4

Breakthrough Curves on Strong Cation Exchange Adsorbers With Sulfonic Acid Ligands on Application of Sodium Hydroxide Solution A commercially available membrane of the Sartobind® S type, a strong cation exchanger, order No. 94IEXS 42-001, from Sartorius Stedim Biotech GmbH, was installed into a housing as described in Example 1 and used. The following steps were performed:
1. Rinsing of the adsorbent with 10 ml of a solution of 1 mol/l HCl in water.
2. Washing of the adsorbent with 40 ml of high purity water.
3. Application of a 2 mmol/l NaOH solution onto the adsorber.
4. Recording of the volume passed and the pH in the outflow by means of a flow cell for the pH.

FIG. 4 shows the breakthrough curve of a 3-layer ion strong cation exchange adsorber stack with sulfonic acid ligands in which an artificial defect (hole) had been introduced, compared to an intact stack, on application of sodium hydroxide solution. A markedly earlier breakthrough is seen for the membrane stack with hole compared to the intact membrane stack.

| List of Reference Symbols | |
|---|---|
| 1 | 29 |
| 2 | 30 |
| 3 | 31 |
| 4 | 32 |
| 5 | 33 |
| 6 | 34 |
| 7 | 35 |
| 8 | 36 |
| 9 | 37 |
| 10 | 38 |
| 11 | 39 |
| 12 | 40 |
| 13 | 41 |
| 14 | 42 |
| 15 | 43 |
| 16 | 44 |
| 17 | 45 |
| 18 | 46 |
| 19 | 47 |
| 20 | 48 |
| 21 | 49 |
| 22 | 50 |
| 23 | 51 |
| 24 | 52 |
| 25 | 53 |
| 26 | 54 |
| 27 | 55 |
| 28 | 56 |

The invention claimed is:

1. A method for validation of a non-particulate anion exchange adsorber, with anion-exchanging groups, comprising the steps of
   loading the non-particulate adsorber with alkali solution,
   rinsing the non-particulate anion exchange adsorber with water,
   loading the adsorber with a liquid, ion-containing acid and detecting a concentration of the ions that have broken through by means of an ion-sensitive probe to determine a concentration profile, and
   comparing the determined concentration profile with a concentration profile of a non-particulate ion exchange adsorber of known integrity.

2. A method for validation of a non-particulate cation exchange adsorber, with cation-exchanging groups, comprising the steps of
   loading the non-particulate adsorber with acid,
   rinsing the non-particulate ion exchange adsorber with water,
   loading the adsorber with a liquid, ion-containing alkali solution and detecting a concentration of the ions that have broken through by means of an ion-sensitive probe to determine a concentration profile, and
   comparing the determined concentration profile with a concentration profile of a non-particulate ion exchange adsorber of known integrity.

3. The method of claim 2, wherein the ion-sensitive probe is a pH electrode, an ion-sensitive field effect transistor or a pH indicator dye.

4. The method of claim 1, wherein the ion-sensitive probe is a pH electrode, an ion-sensitive field effect transistor or a pH indicator dye.

* * * * *